US006365727B1

(12) United States Patent
Yoon et al.

(10) Patent No.: US 6,365,727 B1
(45) Date of Patent: Apr. 2, 2002

(54) DNA AND PEPTIDES OF A DIABETES-SPECIFIC ENDOGENOUS RETROVIRUS

(75) Inventors: Ji-Won Yoon; Hee-Sook Jun, both of Alberta (CA); Hae-Joon Park; Jong Seong Ahn, both of Yongin-si (KR); Young-Ju Ha, Seoul (KR); Soo-Il Chung, Sungnam-si (KR)

(73) Assignee: Green Cross Vaccine Corporation, Kyonggi-do (KR)

( * ) Notice: Subject to any disclaimer, the term of this patent is extended or adjusted under 35 U.S.C. 154(b) by 0 days.

(21) Appl. No.: 09/120,653

(22) Filed: Jul. 22, 1998

(30) Foreign Application Priority Data

Mar. 24, 1998 (KR) ............................................ 98-10108

(51) Int. Cl.[7] .............................................. C07H 21/04
(52) U.S. Cl. ............................... 536/23.72; 424/187.1; 424/207.1
(58) Field of Search ..................... 536/23.72; 424/187.1, 424/207.1

(56) References Cited

PUBLICATIONS

Strongin, W., 1993, "Sensitivity, Specificity, and Predictive Value of Diagnostic Tests: Definitions and Clinical Applications", in Laboratory Diagnosis of Viral Infections, Lennette, E., ed., Marcel Dekker, Inc., New York, pp. 211–219.*
Kim, A., et al., 1999, "Human endogenous retrovirus with a high genomic sequence homology with IDDMK1,222 is not specific for Type I (insulin–dependent) diabetic patients but ubiquitous." Diabetologia, 42 (4):413–8 (abstract provided).*
Bosi, E., and E. Sarugeri, 1998, "Advances and controversies in etiopathogenesis of type 1 (insulin–dependent) diabetes mellitus." Journal of Pediatric Endocrinology and Metabolism, 11(Suppl 2): 293–305 (abstract provided).*
Badenhoop, K., et al., 1999, "IDDM patients neither show humoral reactivities against endogenous retroviral envelope protein nor do they differ in retroviral mRNA expression from healthy relatives or normal individuals.", Diabetes, 48(1):215–8 (abstract provided).*
Rapid Publication—Diabetes, vol. 37, Dec. 1988, pp. 1722–1726, By Kenji Suenaga and Ji–Won Yoon.
Autoimmunity, 1995, vol. 20, pp. 19–24, By Chin Y. Pak, Hee Sook Jun, Millina Lee and Ji–Won Yoon.
Diabetes, vol. 39, Oct. 1990, By Sung–Hee, Ihm and Ji–Won Yoon.

* cited by examiner

*Primary Examiner*—Laurie Scheiner
*Assistant Examiner*—Jeffrey S. Parkin
(74) *Attorney, Agent, or Firm*—Bachman & LaPointe, P.C.

(57) ABSTRACT

The present invention relates to gene and peptide sequences of a diabetes-specific endogenous retrovirus which is derived from type 1 diabetes patients. In particular, the present invention relates to a whole genome of the diabetes-specific variant of endogenous retrovirus (ERV-9) purified from pancreatic tissues of type 1 diabetes (insulin-dependent diabetes mellitus [IDDM]) patients and its genes and peptide and their sequences, which can be used as a diagnosing reagent for type 1 diabetes and as an immunogen.

The diabetes-specific retrovirus expressed exclusively in pancreatic beta cells was purified from deceased type 1 diabetes patients. Subsequently, the retroviral gene sequences were determined, and by analyzing the amino acid sequence of the peptide deduced from the gene, 21 domains of the peptide having hydrophilicity and immunodominancy were identified.

Therefore, the variant gene of the endogenous retrovirus and the peptide deduced from the gene can be effectively used as a diagnosing reagent of autoimmune-antibody for type 1 diabetes and as a vaccine for the variant ERV-9 related diseases.

4 Claims, 2 Drawing Sheets

SEQUENCE LISTING

<160> NUMBER OF SEQ ID NOS:   28

<210> SEQ ID NO 1
<211> LENGTH: 3910
<212> TYPE: DNA
<213> ORGANISM: DIABETES-SPECIFIC ENDOGENOUS RETROVIRUS ERV-9

<400> SEQUENCE: 1
cggagaaagc tccaaaagca agccctgggc cctgaacaaa atctggaggc attattaaac    60

-continued

```
ctggcaacct tagtgttcta taatagggtc cgagaggaac aggcccaaaa ggaaaagtga      120
gatcagagag aggccacagc cttagtcatg gccctcagac aaacaaacct tggtggttca      180
gagaggacag aaaatggatc aggccaatca cctggtaggg cttgttatca gtgtggttta      240
caaggacact ttaaaaaaga ttgtccaaca agaaacaagc cacccctca tccatgtccg       300 ctatgccgag ccaatcactg gaaggcacac tgccccagag tgaaatggtt ctctggccca      360
gaagccctca accagatgat ccaacaacag gactgagagt gcctgggcca agtgccagct      420
catgtcatca accttactga gtcccgggta tgtttaacca ttgagggcca ggaaattgac      480
ttcctcctgg acactggcat ggccttctca gtgttaatct cctgtcctgg atgactgtcc      540
tcaaggtcca ttaccatcca aggaatccta agacagccta taccaggta tttctcccac       600 ctcctcagtt gtaattggga gactttgctc ttttcacatg cctttcttgt tatacctgaa      660
agtcccacac cctattaggg agggatata ttagccaaag ctggagctat tacctatatg       720
aataagagga acaagttaac catttgttgt cctctacttg aggagggaat caaccctgaa      780
gtctgggcat tggaaggaca atttggaagg gcaaaaaatg cctgcccagt ccaaatcagg      840
ctaaaagacc ccaccacttt tcctatcaaa ggcaatatcc cttaaggcct gaagctcata      900
aaggattaca ggatattgct gaacatttaa tagctcaagg cttagtaagg aaatgcagca      960
gtccctgaaa cacgccaatt ctaggagtac aaaaaccgaa cggtcagtgg agactagtgc     1020
aagatcttag actcactaat gacgcagtaa ttcctctata tccagttgta cccaacccct     1080
ataccctgct ctctcaaata ccagaggaag cagaatggtt cacagttctg gacttcaagg     1140
atgccttctt ctgtgttccc ctgcactctg attcacagct cctctttgct tttgaggatc     1200
ccacaaacca cacatcccaa cttacatgga tggtcttgcc ccaagggttt agggatagcc     1260
ctcatctgtt tggtcaggcc ctagccaaag atctaagcca cttctcaggt ccaggcactc     1320
tggtccttca atatgtggat gatttacttt tggctaccag ttaggaagcc ttgtgccagc     1380
aggctactct agatctcttg aaccttctag ctaatcaagg gtacaaggtg tctatgttca     1440
aagcccaact ttgcctacag caggttaaat atctaggcct aatcttagcc aaagggacaa     1500
gggccctcag caaggaatga atacagccta tactggctta tcctcgccct aagacattaa     1560
aacagttgag ggagttcctt ggaattacca gcttttgccg actatggatc cctggataca     1620
gcgagacagc caggcccctc taatcaagga acccagagg gcaaatactc atctagttga      1680
gtgggaacca gaggcagaaa caaccttcag aaccttaaag caggctctag tacaagctcc     1740
agctttaagc tttcccacag gacagaattt ctctttatat gtcagagaga gagccaggat     1800
agctattaga gtcctcactc aaactcatcg gactgcccca cgaccagtgg caaacctaag     1860
taaggaaatt gatgtagtag caaaaggctg gcctcagtgt ttaggggtag ttgcagctgt     1920
ggccgcctta gcatcagagg ctatcaaaat aatacaagga aaggatctca cagtctagac     1980
tacttatgat gttaatggca tactaggtgc ccaaggaagt ttatggctat cagataactg     2040
cctacttaga taccaggcac tactccttga gggaacagta cttaaaaaat gcacatgcat     2100
ggcccttaac cctgccactt ttctcacaga ggatcgggaa cctatcaagc aggactgaca     2160
acaaattata gtccagactt atgccgcccg agatgatctc ttaaaagtcc ccttaactaa     2220
tccagacctt aacctatata ctgatggaag ttcacttgtg gaccatgcga tacgtaggtt     2280
agttatgtaa cgatacttga aaacaagcct cttccgccag ggaccagtgc ccagttagcg     2340
gaactagtgg cacttacctt ggcctcagaa gtgggatggg caaaagaata aatttgttta     2400
```

-continued

```
gagatagcag gtatgcttat ctaatcctac atgcccatgc tgcaatttgg aaagagagcg      2460
agttcctaac ctctgtagga accccccatta attaccacaa ggaaattata gagttattgc     2520
acgcaatgca aaaacacaaa gaggtcggaa tcttacactg tcaaagccat cagaatagga     2580
acgagagggg agaacagcag cataagcatc tggcagaggt agccgaaaga aaagaaagag     2640
acaggaagtc aaagaaagag acggagagga aaagacaaga agctaaagag aaagacggac     2700
agacacggta gtaaaagaca gggtaaataa gagacgaaga gagaaagaag atgtcaaaga     2760
gacagatgaa gtagtaaaga aaaaacaggt acctattcct ttaaaaccca gggtaaattt     2820
ctctctaccg acgcaaggca attctctatg tgatatcacc catatctgcc tctctaatag     2880
ttgaagaata atgaaatctg tccttacttt acaatccaaa atagacactt tggcagcagt     2940
gactcgccaa aaccgctgag gcatagatgt cctcactgct gaagaaagag gactctgcac     3000
tttcttaggg gaagagtgtt gttttgacac taaccaggca cggatagcat gagatggcac     3060
ccagcgttta cagaaaaagg ctgctgaaat gagtcgcctt ttaaattctt ataccaacct     3120
gtggtgtggg gcaacatggc ttctcacctt tctaggtccc gtggcaaccg tcttggtgtt     3180
actcgccttt gggcccagca tttttaacgt tcttgtcaaa tttgtttgtc tagattcgag     3240
gccttcaagc tacagatggt cttacatatc aaaccccgaa taatttcaac taactacttc     3300
tacggaggac acctggacta accagctggc agttaccctg gcctagagag ttcccctctg     3360
aaggtcacta caactgcaaa gccccttttt cgcgcctatc catcaggacg tacctagaac     3420
agtcctcggc catattgcca acagcagttg gagtgtcctg ttgattgagg ggtgacagca     3480
tgctggcagt cctcacagca ctaacgcgct cgctcacgct cggcacctcc tgtgtctggg     3540
ctcccacttt ggcagcactt gaggagccct tcagctcagt atctacctac tctgatgggt     3600
ccttcgagaa gctttatgtc tagctcaggg cttctaaata gaccaatcaa caccctgtgt     3660
ctagctcagg gcttgtgaat gcgcgaatgg ccacactgta tcttgctact ctagtggggc     3720
cttggagaac ctatgtgtca acgctctgga tctaactaac ctggtccgga tgtgccgaac     3780
cttagtgtct tgctcacgga tgtaaacgga ccaatcaatg ccctgtcaaa ccactcggct     3840
ctaccaatca gcaggatgtg ggtggggcca gataagacaa taacagcagg ctgcccgagc     3900
ctgccgtggc                                                             3910
```

```
<210> SEQ ID NO 2
<211> LENGTH: 396
<212> TYPE: DNA
<213> ORGANISM: DIABETES-SPECIFIC ENDOGENOUS RETROVIRUS ERV-9

<400> SEQUENCE: 2
cggagaaagc tccaaaagca agccctgggc cctgaacaaa atctggaggc attattaaac      60
ctggcaacct tagtgttcta taatagggtc cgagaggaac aggcccaaaa ggaaaagtga     120
gatcagagag aggccacagc cttagtcatg gccctcagac aaacaaacct tggtggttca     180
gagaggacaa aaaatggatc aggccaatca cctggtaggg cttgttatca gtgtggttta     240
caaggacact ttaaaaaaga ttgtccaaca agaaacaagc caccccctca tccatgtccg     300
ctatgccgag ccaatcactg gaaggcacac tgccccagag tgaaatggtt ctctggccca     360
gaagccctca accagatgat ccaacaacag gactga                                396
```

```
<210> SEQ ID NO 3
<211> LENGTH: 131
<212> TYPE: PRT
<213> ORGANISM: DIABETES-SPECIFIC RETROVIRUS ENDOGENOUS ERV-9
```

-continued

```
<220> FEATURE:
<221> NAME/KEY: NON_CONS
<222> LOCATION: (40)
<223> OTHER INFORMATION: any one of 20 amino acids

<400> SEQUENCE: 3

Arg Arg Lys Leu Gln Lys Gln Ala Leu Gly Pro Glu Gln Asn Leu Glu
 1               5                  10                  15

Ala Leu Leu Asn Leu Ala Thr Leu Val Phe Tyr Asn Arg Val Arg Glu
            20                  25                  30

Glu Gln Ala Gln Lys Glu Lys Xaa Asp Gln Arg Glu Ala Thr Ala Leu
        35                  40                  45

Val Met Ala Leu Arg Gln Thr Asn Leu Gly Gly Ser Glu Arg Thr Glu
    50                  55                  60

Asn Gly Ser Gly Gln Ser Pro Gly Arg Ala Cys Tyr Gln Cys Gly Leu
65                  70                  75                  80

Gln Gly His Phe Lys Lys Asp Cys Pro Thr Arg Asn Lys Pro Pro Pro
                85                  90                  95

His Pro Cys Pro Leu Cys Arg Ala Asn His Trp Lys Ala His Cys Pro
            100                 105                 110

Arg Val Lys Trp Phe Ser Gly Pro Glu Ala Leu Asn Gln Met Ile Gln
        115                 120                 125

Gln Gln Asp
    130

<210> SEQ ID NO 4
<211> LENGTH: 2330
<212> TYPE: DNA
<213> ORGANISM: DIABETES-SPECIFIC ENDOGENOUS RETROVIRUS ERV-9

<400> SEQUENCE: 4
gagtgcctgg gccaagtgcc agctcatgtc atcaacctta ctgagtcccg ggtatgttta      60
accattgagg gccaggaaat tgacttcctc ctggacactg gcatggcctt ctcagtgtta     120
atctcctgtc ctggatgact gtcctcaagg tccattacca tccaaggaat cctaagacag     180
cctataacca ggtatttctc ccacctcctc agttgtaatt gggagacttt gctcttttca     240
catgcctttc ttgttatacc tgaaagtccc acacccttat tagggaggga tatattagcc     300
aaagctggag ctattaccta tatgaataag aggaacaagt taaccatttg ttgtcctcta     360
cttgaggagg gaatcaaccc tgaagtctgg gcattggaag acaatttggg aagggcaaaa     420
aatgcctgcc cagtccaaat caggctaaaa gaccccacca cttttcctat caaaggcaat     480 atccccttaag gcctgaagct cataaaggat tacaggatat tgctagacat ttaatagctc     540
aaggcttagt aaggaaatgc agcagtccct gaaacacgcc aattctagga gtacaaaaac     600
cgaacggtca gtggagacta gtgcaagatc ttagactcac taatgacgca gtaattcctc     660
tatatccagt tgtacccaac ccctataccc tgctctctca ataccagag gaagcagaat     720 ggttcacagt tctggacttc aaggatgcct tcttctgtgt tccccctgcac tctgattcac     780 agctcctctt tgcttttgag gatcccacaa accacacatc ccaacttaca tggatggtct     840
tgccccaagg gttagggat agccctcatc tgtttggtca ggccctagcc aaagatctaa     900
gccacttctc aggtccaggc actctggtcc ttcaatatgt ggatgattta cttttggcta     960
ccagttagga agccttgtgc cagcaggcta ctctagatct cttgaacctt ctagctaatc    1020
aagggtacaa ggtgtctatg ttcaaagccc aactttgcct acagcaggtt aaatatctag    1080
gcctaatctt agccaaaggg acaagggccc tcagcaagga atgaatacag cctatactgg    1140
```

```
cttatcctcg ccctaagaca ttaaaacagt tgagggagtt ccttggaatt accagctttt   1200
gccgactatg gatccctgga tacagcgaga cagccaggcc cctctaatca aggaaaccca   1260
gagggcaaat actcatctag ttgagtggga accagaggca gaaacaacct tcagaacctt   1320
aaagcaggct ctagtacaag ctccagcttt aagctttccc acaggacaga atttctcttt   1380
atatgtcaga gagagagcca ggatagctat tagagtcctc actcaaactc atcggactgc   1440
cccacgacca gtggcaaacc taagtaagga aattgatgta gtagcaaaag gctggcctca   1500
gtgtttaggg gtagttgcag ctgtggccgc cttagcatca gaggctatca aaataataca   1560
aggaaaggat ctcacagtct agactactta tgatgttaat ggcatactag gtgcccaagg   1620
aagtttatgg ctatcagata actgcctact tagataccag gcactactcc ttgagggaac   1680
agtacttaaa aaatgcacat gcatggccct taaccctgcc acttttctca cagaggatcg   1740
ggaacctatc aagcaggact gacaacaaat tatagtccag acttatgccg cccgagatga   1800
tctcttaaaa gtccccttaa ctaatccaga ccttaaccta tatactgatg gaagttcact   1860
tgtggaccat gcgatacgta ggttagttat gtaacgatac ttgaaaacaa gcctcttccg   1920
ccagggacca gtgcccagtt agcggaacta gtggcactta ccttggcctc agaagtggga   1980
tgggcaaaag aataaatttg tttagagata gcaggtatgc ttatctaatc ctacatgccc   2040
atgctgcaat ttggaaagag agcgagttcc taacctctgt aggaaccccc attaattacc   2100
acaaggaaat tatagagtta ttgcacgcaa tgcaaaaaca caaagaggtc ggaatcttac   2160
actgtcaaag ccatcagaat aggaacgaga ggggagaaca gcagcataag catctggcag   2220
aggtagccga aagaaaagaa agagacagga agtcaaagaa agagacggag aggaaaagac   2280
aagaagctaa agagaaagac ggacagacac ggtagtaaaa gacagggtaa              2330
```

<210> SEQ ID NO 5
<211> LENGTH: 768
<212> TYPE: PRT
<213> ORGANISM: DIABETES-SPECIFIC ENDOGENOUS RETROVIRUS ERV-9
<220> FEATURE:
<221> NAME/KEY: NON_CONS
<222> LOCATION: (46)
<223> OTHER INFORMATION: any one of amino acids
<221> NAME/KEY: NON_CONS
<222> LOCATION: (193)
<223> OTHER INFORMATION: any one of amino acids
<221> NAME/KEY: NON_CONS
<222> LOCATION: (322)
<223> OTHER INFORMATION: any one of amino acids
<221> NAME/KEY: NON_CONS
<222> LOCATION: (374)
<223> OTHER INFORMATION: any one of amino acids
<221> NAME/KEY: NON_CONS
<222> LOCATION: (526)
<223> OTHER INFORMATION: any one of amino acids
<221> NAME/KEY: NON_CONS
<222> LOCATION: (586)
<223> OTHER INFORMATION: any one of amino acids

<400> SEQUENCE: 5

```
Glu Cys Leu Gly Gln Val Pro Ala His Val Ile Asn Leu Thr Glu Ser
 1               5                  10                  15

Arg Val Cys Leu Thr Ile Glu Gly Gln Glu Ile Asp Phe Leu Leu Asp
                20                  25                  30

Thr Gly Met Ala Phe Ser Val Leu Ile Ser Cys Pro Gly Xaa Leu Ser
            35                  40                  45

Ser Arg Ser Ile Thr Ile Gln Gly Ile Leu Arg Gln Pro Ile Thr Arg
        50                  55                  60
```

```
Tyr Phe Ser His Leu Leu Ser Cys Asn Trp Glu Thr Leu Leu Phe Ser
 65                  70                  75                  80

His Ala Phe Leu Val Ile Pro Glu Ser Pro Thr Pro Leu Leu Gly Arg
                 85                  90                  95

Asp Ile Leu Ala Lys Ala Gly Ala Ile Thr Tyr Met Asn Lys Arg Asn
                100                 105                 110

Lys Leu Thr Ile Cys Cys Pro Leu Leu Glu Arg Glu Ser Thr Leu Lys
            115                 120                 125

Ser Gly His Trp Lys Asp Asn Leu Glu Gly Gln Lys Met Pro Ala Gln
130                 135                 140

Ser Lys Ser Gly Lys Arg Pro His His Phe Ser Tyr Gln Arg Gln Tyr
145                 150                 155                 160

Pro Leu Arg Pro Glu Ala His Lys Gly Leu Gln Asp Ile Ala Glu His
                165                 170                 175

Leu Ile Ala Gln Gly Leu Val Arg Lys Cys Ser Ser Pro Asn Thr Pro
                180                 185                 190

Xaa Ile Leu Gly Val Gln Lys Pro Asn Gly Gln Trp Arg Leu Val Gln
            195                 200                 205

Asp Leu Arg Leu Thr Asn Asp Ala Val Ile Pro Leu Tyr Pro Val Val
210                 215                 220

Pro Asn Pro Tyr Thr Leu Leu Ser Gln Ile Pro Glu Glu Ala Glu Trp
225                 230                 235                 240

Phe Thr Val Leu Asp Phe Lys Asp Ala Phe Phe Cys Val Pro Leu His
                245                 250                 255

Ser Asp Ser Gln Leu Leu Phe Ala Phe Glu Asp Pro Thr Asn His Thr
                260                 265                 270

Ser Gln Leu Thr Trp Met Val Leu Pro Gln Gly Phe Arg Asp Ser Pro
            275                 280                 285

His Leu Phe Gly Gln Ala Leu Ala Lys Asp Leu His Phe Ser Gly
            290                 295                 300

Pro Gly Thr Leu Val Leu Gln Tyr Val Asp Asp Leu Leu Leu Ala Thr
305                 310                 315                 320

Ser Xaa Glu Ala Leu Cys Gln Gln Ala Thr Leu Asp Leu Leu Asn Leu
                325                 330                 335

Leu Ala Asn Gln Gly Tyr Lys Val Ser Met Phe Lys Ala Gln Leu Cys
                340                 345                 350

Leu Gln Gln Val Lys Tyr Leu Gly Leu Ile Leu Ala Lys Gly Thr Arg
            355                 360                 365

Ala Leu Ser Lys Glu Xaa Ile Gln Pro Ile Leu Ala Tyr Pro Arg Pro
370                 375                 380

Lys Thr Leu Lys Gln Leu Arg Glu Phe Leu Gly Ile Thr Ser Phe Cys
385                 390                 395                 400

Arg Leu Trp Ile Pro Gly Tyr Ser Glu Thr Ala Arg Pro Leu Ile Lys
                405                 410                 415

Glu Thr Gln Arg Ala Asn Thr His Leu Val Glu Trp Glu Pro Glu Ala
                420                 425                 430

Glu Thr Thr Phe Arg Thr Leu Lys Gln Ala Leu Val Gln Ala Pro Ala
            435                 440                 445

Leu Ser Phe Pro Thr Gly Gln Asn Phe Ser Leu Tyr Val Arg Glu Arg
                450                 455                 460

Ala Arg Ile Ala Ile Arg Val Leu Thr Gln Thr His Arg Thr Ala Pro
465                 470                 475                 480
```

Arg Pro Val Ala Asn Leu Ser Lys Glu Ile Asp Val Val Ala Lys Gly
            485                 490                 495

Trp Pro Gln Cys Leu Gly Val Ala Ala Val Ala Ala Leu Ala Ser
            500                 505                 510

Glu Ala Ile Lys Ile Ile Gln Gly Lys Asp Leu Thr Val Xaa Thr Thr
            515                 520                 525

Tyr Asp Val Asn Gly Ile Leu Gly Ala Gln Gly Ser Leu Trp Leu Ser
530                 535                 540

Asp Asn Cys Leu Leu Arg Tyr Gln Ala Leu Leu Glu Gly Thr Val
545                 550                 555                 560

Leu Lys Lys Cys Thr Cys Met Ala Leu Asn Pro Ala Thr Phe Leu Thr
                565                 570                 575

Glu Asp Arg Glu Pro Ile Lys Gln Asp Xaa Gln Gln Ile Ile Val Gln
            580                 585                 590

Thr Tyr Ala Ala Arg Asp Asp Leu Leu Lys Val Pro Leu Thr Asn Pro
            595                 600                 605

Asp Leu Asn Leu Tyr Thr Asp Gly Ser Ser Leu Val Asp His Ala Ile
            610                 615                 620

Arg Val Ser Tyr Val Thr Ile Leu Glu Asn Lys Pro Leu Pro Pro Gly
625                 630                 635                 640

Thr Ser Ala Gln Leu Ala Glu Leu Val Ala Leu Thr Leu Ala Ser Glu
                645                 650                 655

Val Gly Gly Lys Arg Ile Asn Leu Phe Arg Asp Ser Arg Tyr Ala Tyr
                660                 665                 670

Leu Ile Leu His Ala His Ala Ala Ile Trp Lys Glu Ser Glu Phe Leu
            675                 680                 685

Thr Ser Val Gly Thr Pro Ile Asn Tyr His Lys Glu Ile Ile Glu Leu
            690                 695                 700

Leu His Ala Met Gln Lys His Lys Glu Val Gly Ile Leu His Cys Gln
705                 710                 715                 720

Ser His Gln Asn Arg Asn Glu Arg Gly Glu Gln Gln His Lys His Leu
                725                 730                 735

Ala Glu Val Ala Glu Arg Lys Glu Arg Asp Arg Lys Ser Lys Lys Glu
            740                 745                 750

Thr Glu Arg Lys Arg Gln Glu Ala Lys Glu Lys Asp Gly Gln Thr Arg
            755                 760                 765

<210> SEQ ID NO 6
<211> LENGTH: 464
<212> TYPE: DNA
<213> ORGANISM: DIABETES-SPECIFIC ENDOGENOUS RETROVIRUD ERV-9

<400> SEQUENCE: 6
acccatatct gcctctctaa tagttgaaga ataatgaaat ctgtccttac tttacaatcc      60
aaaatagaca ctttggcagc agtgactcgc caaaaccgct gaggcataga tgtcctcact     120
gctgaagaaa gaggactctg cactttctta ggggaagagt gttgttttga cactaaccag     180
gcacggatag catgagatgg cacccagcgt ttacagaaaa aggctgctga aatgagtcgc     240
cttttaaatt cttataccaa cctgtggtgt ggggcaacat ggcttctcac ctttctaggt     300
cccgtggcaa ccgtcttggt gttactcgcc tttgggccca gcattttttaa cgttcttgtc     360
aaatttgttt gtctagattc gaggccttca agctacagat ggtcttacat atcaaaccccc    420
gaataatttc aactaactac ttctacggag gacacctgga ctaa                      464

```
<210> SEQ ID NO 7
<211> LENGTH: 152
<212> TYPE: PRT
<213> ORGANISM: DIABETES-SPECIFIC ENDOGENOUS RETEOVIRUS ERV-9
<220> FEATURE:
<221> NAME/KEY: NON_CONS
<222> LOCATION: (33)
<223> OTHER INFORMATION: any one of amino acids
<221> NAME/KEY: NON_CONS
<222> LOCATION: (64)
<223> OTHER INFORMATION: any one of amino acids

<400> SEQUENCE: 7

Thr His Ile Cys Leu Ser Asn Ser Glu Glu Met Lys Ser Val Leu Thr
 1               5                  10                  15

Leu Gln Ser Lys Ile Asp Thr Leu Ala Ala Val Thr Arg Gln Asn Arg
            20                  25                  30

Xaa Gly Ile Asp Val Leu Thr Ala Glu Glu Arg Gly Leu Cys Thr Phe
        35                  40                  45

Leu Gly Glu Glu Cys Cys Phe Asp Thr Asn Gln Ala Arg Ile Ala Xaa
    50                  55                  60

Asp Gly Thr Gln Arg Leu Gln Lys Lys Ala Ala Glu Met Ser Arg Leu
65                  70                  75                  80

Leu Asn Ser Tyr Thr Asn Leu Trp Cys Gly Ala Thr Trp Leu Leu Thr
                85                  90                  95

Phe Leu Gly Pro Val Ala Thr Val Leu Val Leu Ala Phe Gly Pro
            100                 105                 110

Ser Ile Phe Asn Val Leu Val Lys Phe Val Ser Arg Phe Glu Ala Phe
        115                 120                 125

Lys Leu Gln Met Val Leu His Ile Lys Pro Arg Ile Ile Ser Thr Asn
    130                 135                 140

Tyr Phe Tyr Gly Gly His Leu Asp
145                 150

<210> SEQ ID NO 8
<211> LENGTH: 16
<212> TYPE: PRT
<213> ORGANISM: DIABETES-SPECIFIC ENDOGENOUS RETROVIRUS ERV-9

<400> SEQUENCE: 8

Arg Arg Lys Leu Gln Lys Gln Ala Leu Gly Pro Glu Gln Asn Leu Glu
 1               5                  10                  15

<210> SEQ ID NO 9
<211> LENGTH: 16
<212> TYPE: PRT
<213> ORGANISM: DIABETES-SPECIFIC ENDOGENOUS RETROVIRUS ERV-9
<220> FEATURE:
<221> NAME/KEY: NON_CONS
<222> LOCATION: (12)
<223> OTHER INFORMATION: any one of amino acids

<400> SEQUENCE: 9

Arg Val Arg Glu Glu Gln Ala Gln Lys Glu Lys Xaa Asp Gln Arg Glu
 1               5                  10                  15

<210> SEQ ID NO 10
<211> LENGTH: 18
<212> TYPE: PRT
<213> ORGANISM: DIABETS-SPECIFIC ENDOGENOUS RETROVIRUS ERV-9

<400> SEQUENCE: 10

Gly Gly Ser Glu Arg Thr Glu Asn Gly Ser Gly Gln Ser Pro Gly Arg
```

-continued

```
                1               5                  10                 15

Ala Cys

<210> SEQ ID NO 11
<211> LENGTH: 24
<212> TYPE: PRT
<213> ORGANISM: DIEBETES-SPECIFIC ENDOGENOUS RETROVIRUS ERV-9

<400> SEQUENCE: 11

Lys Lys Asp Cys Pro Thr Arg Asn Lys Pro Pro Pro His Pro Cys Pro
 1               5                  10                 15

Leu Cys Arg Ala Asn His Trp Lys
            20

<210> SEQ ID NO 12
<211> LENGTH: 32
<212> TYPE: PRT
<213> ORGANISM: DIABETES-SPECIFIC ENDOGENOUS RETROVIRUS ERV-9

<400> SEQUENCE: 12

Glu Arg Glu Ser Thr Leu Lys Ser Gly His Trp Lys Asp Asn Leu Glu
 1               5                  10                 15

Gly Gln Lys Met Pro Ala Gln Ser Lys Ser Gly Lys Arg Pro His His
            20                  25                  30

<210> SEQ ID NO 13
<211> LENGTH: 22
<212> TYPE: PRT
<213> ORGANISM: DIABETES-SPECIFIC ENDOGENOUS RETROVIRUS ERV-9

<400> SEQUENCE: 13

Ser Tyr Gln Arg Gln Tyr Pro Leu Arg Pro Glu Ala His Lys Gly Leu
 1               5                  10                 15

Gln Asp Ile Ala Glu His
            20

<210> SEQ ID NO 14
<211> LENGTH: 25
<212> TYPE: PRT
<213> ORGANISM: DIABETES-SPECIFIC ENDOGENOUS RETROVIRUS ERV-9
<220> FEATURE:
<221> NAME/KEY: NON_CONS
<222> LOCATION: (10)
<223> OTHER INFORMATION: any one of amino acids

<400> SEQUENCE: 14

Gly Leu Val Arg Lys Cys Ser Ser Pro Xaa Asn Thr Pro Ile Leu Gly
 1               5                  10                 15

Val Gln Lys Pro Asn Gly Gln Trp Arg
            20                  25

<210> SEQ ID NO 15
<211> LENGTH: 22
<212> TYPE: PRT
<213> ORGANISM: DIABETES-SPECIFIC ENDOGENOUS RETROVIRUS ERV-9

<400> SEQUENCE: 15

His Ser Asp Ser Gln Leu Leu Phe Ala Phe Glu Asp Pro Thr Asn His
 1               5                  10                 15

Thr Ser Gln Leu Thr Trp
            20
```

```
<210> SEQ ID NO 16
<211> LENGTH: 22
<212> TYPE: PRT
<213> ORGANISM: DIABETES-SPECIFIC ENDOGENOUS RETROVIRUS ERV-9

<400> SEQUENCE: 16

Arg Asp Ser Pro His Leu Phe Gly Gln Ala Leu Ala Lys Asp Leu Ser
 1               5                  10                  15

His Phe Ser Gly Pro Gly
            20

<210> SEQ ID NO 17
<211> LENGTH: 16
<212> TYPE: PRT
<213> ORGANISM: DIABETES-SPECIFIC ENDOGENOUS RETROVIRUS ERV-9

<400> SEQUENCE: 17

Lys Asp Leu Ser His Phe Ser Gly Pro Gly Thr Leu Val Leu Gln Tyr
 1               5                  10                  15

<210> SEQ ID NO 18
<211> LENGTH: 22
<212> TYPE: PRT
<213> ORGANISM: DIABETES-SPECIFIC ENDOGENOUS RETROVIRUS ERV-9
<220> FEATURE:
<221> NAME/KEY: NON_CONS
<222> LOCATION: (4)
<223> OTHER INFORMATION: any one of amino acids

<400> SEQUENCE: 18

Ser Lys Glu Xaa Ile Gln Pro Ile Leu Ala Tyr Pro Arg Pro Lys Thr
 1               5                  10                  15

Leu Lys Gln Leu Arg Glu
            20

<210> SEQ ID NO 19
<211> LENGTH: 30
<212> TYPE: PRT
<213> ORGANISM: DIABETES-SPECIFIC ENDOGENOUS RETROVIRUS ERV-9

<400> SEQUENCE: 19

Arg Pro Leu Ile Lys Glu Thr Gln Arg Ala Asn Thr His Leu Val Glu
 1               5                  10                  15

Trp Glu Pro Glu Ala Glu Thr Thr Phe Arg Thr Leu Lys Gln
            20                  25                  30

<210> SEQ ID NO 20
<211> LENGTH: 22
<212> TYPE: PRT
<213> ORGANISM: DIEBETES-SPECIFIC ENDOGENOUS RETROVIRUS ERV-9

<400> SEQUENCE: 20

Arg Val Leu Thr Gln Thr His Arg Thr Ala Pro Arg Pro Val Ala Asn
 1               5                  10                  15

Leu Ser Lys Glu Ile Asp
            20

<210> SEQ ID NO 21
<211> LENGTH: 23
<212> TYPE: PRT
<213> ORGANISM: DIABETES-SPECIFIC ENDOGENOUS RETROVIRUS ERV-9
<220> FEATURE:
<221> NAME/KEY: NON_CONS
<222> LOCATION: (17)
<223> OTHER INFORMATION: any one of amino acids
```

-continued

```
<400> SEQUENCE: 21

Asn Pro Ala Thr Phe Leu Thr Glu Asp Arg Glu Pro Ile Lys Gln Asp
  1               5                  10                  15

Xaa Gln Gln Ile Ile Val Gln
             20

<210> SEQ ID NO 22
<211> LENGTH: 22
<212> TYPE: PRT
<213> ORGANISM: DIEBETES-SPECIFIC ENDOGENOUS RETROVIRUS ERV-9

<400> SEQUENCE: 22

Arg Asp Asp Leu Leu Lys Val Pro Leu Thr Asn Pro Asp Leu Asn Leu
  1               5                  10                  15

Tyr Thr Asp Gly Ser Ser
             20

<210> SEQ ID NO 23
<211> LENGTH: 15
<212> TYPE: PRT
<213> ORGANISM: DIEBETES-SPECIFIC ENDOGENOUS RETROVIRUS ERV-9

<400> SEQUENCE: 23

Ser Glu Val Gly Gly Lys Arg Ile Asn Leu Phe Arg Asp Ser Arg
  1               5                  10                  15

<210> SEQ ID NO 24
<211> LENGTH: 21
<212> TYPE: PRT
<213> ORGANISM: DIEBETES-SPECIFIC ENDOGENOUS RETROVIRUS ERV-9

<400> SEQUENCE: 24

Gly Ile Leu His Cys Gln Ser His Gln Asn Arg Asn Glu Arg Gly Glu
  1               5                  10                  15

Gln Gln His Lys His
             20

<210> SEQ ID NO 25
<211> LENGTH: 31
<212> TYPE: PRT
<213> ORGANISM: DIEBETES-SPECIFIC ENDOGENOUS RETROVIRUS ERV-9

<400> SEQUENCE: 25

Glu Val Ala Glu Arg Lys Glu Arg Asp Arg Lys Ser Lys Lys Glu Thr
  1               5                  10                  15

Glu Arg Lys Arg Gln Glu Ala Lys Glu Lys Asp Gly Gln Thr Arg
             20                  25                  30

<210> SEQ ID NO 26
<211> LENGTH: 17
<212> TYPE: PRT
<213> ORGANISM: DIEBETES-SPECIFIC ENDOGENOUS RETROVIRUS ERV-9

<400> SEQUENCE: 26

Ser Asn Ser Glu Glu Met Lys Ser Val Leu Thr Leu Gln Ser Lys Ile
  1               5                  10                  15

Asp

<210> SEQ ID NO 27
<211> LENGTH: 30
<212> TYPE: PRT
```

-continued

```
<213> ORGANISM: DIEBETES-SPECIFIC ENDOGENOUS RETROVIRUS ERV-9
<220> FEATURE:
<221> NAME/KEY: NON_CONS
<222> LOCATION: (15)
<223> OTHER INFORMATION: any one of amino acids

<400> SEQUENCE: 27

Gly Glu Glu Cys Cys Phe Asp Thr Asn Gln Ala Arg Ile Ala Xaa Asp
 1               5                  10                  15

Gly Thr Gln Arg Leu Gln Lys Lys Ala Ala Glu Met Ser Arg
            20                  25                  30

<210> SEQ ID NO 28
<211> LENGTH: 32
<212> TYPE: PRT
<213> ORGANISM: DIIEBETES-SPECIFIC ENDOGENOUS RETROVIRUS ERV-9

<400> SEQUENCE: 28

Phe Val Ser Arg Phe Glu Ala Phe Lys Leu Gln Met Val Leu His Ile
 1               5                  10                  15

Lys Pro Arg Ile Ile Ser Thr Asn Tyr Phe Tyr Gly Gly His Leu Asp
            20                  25                  30
```

DNA AND PEPTIDES OF A DIABETES-SPECIFIC ENDOGENOUS RETROVIRUS

FIELD OF THE INVENTION

The present invention relates to the gene and peptide sequences of a diabetes-specific endogenous retrovirus derived from type 1 diabetes patients. In particular, the present invention relates to the whole genome of the diabetes-specific variant of endogenous retrovirus (ERV-9) purified from pancreatic tissues of type 1 diabetes (insulin-dependent diabetes mellitus [IDDM]) patients, and viral genes and peptides sequences which can be used to develop a diagnosing reagent for type 1 diabetes and an immunogen.

BACKGROUND OF THE INVENTION

It is known that the human genome contains a complex variety of inherited endogenous retroviral sequences, several of which are transcriptionally active and contain open reading frames. Aberrant expression of endogenous retroviral sequences has been implicated in the pathogenesis of many autoimmune diseases, including Sjogren's syndrome (Hao W., et al., *J. Autoimmune*, 6: 787–798, 1993), rheumatoid arthritis (Garry R. F., *Arthritis and Rheumatism*, 37: 465–469, 1994), systemic lupus erythematosus (Wilder R. L., *Current Opinions in Rheumatology*, 6: 295–299, 1994), Hashimoto's thyroiditis (Blomberg J., et al., *Arthritis and Rheumatism*. 37: 57–66, 1994), Graves' disease (Blomberg J., et al.,*Arthritis and Rheumatism*. 37: 57–66, 1994) and the like. In addition, some infectious exogenous retroviruses cause manifestations of autoimmunity (Tomer Y., et al., *Endocrine Reviews*, 14: 107–120, 1993).

Type 1 diabetes, also known as insulin-dependent diabetes mellitus, is an autoimmune diseases resulting from the destruction of pancreatic beta cells by beta cell-specific autoimmune processes. However, the processes which trigger the autoimmunity remain unknown. In the pancreatic beta cells of non-obese diabetic (NOD) mice, a spontaneously diabetic animal model for human type 1 diabetes, the presence of retrovirus particles in pancreatic beta cells, which is known to be associated with insulitis and diabetes, has been reported. The initiation of insulitis in NOD mice is known to occur at 4 to 6 weeks of age. Fujita et al. observed retrovirus particles in NOD mice as young as 2 days old using electron microscopy (Fujita H., et al., *Biochemical Research*, 5(1): 71–76, 1984). In addition, Serreze et al. found that anti-type C retrovirus antibody shows peak titer shortly after weaning in NOD mice (Serreze D. V., et al., *Diabetes*, 37: 351–358, 1988). In this study, type C retrovirus particles were found in both intact and lymphocyte-infiltrated islets, and retrovirus particles were also detected in beta cells showing severe nuclear damage within intact islets which showed no evidence of lymphocytic infiltration. In another study, Like and Rossini observed the induction of aberrant retrovirus budding into the rough endoplasmic reticulum of the beta cells, two to three days before insulitis developed in male CD-1 mice treated with multiple doses of streptozotocin (Like A. A. and Rossini A. A., *Science*, 193: 415–417, 1976). These results suggest that the expression of retrovirus occurs prior to lymphocytic infiltration of the islets. Thus, the expression of retrovirus has been assumed to be an initial event in the damage of beta cells, rather than the result of insulitis.

To date, there has been no report of the exclusive expression of retrovirus particles in the beta cells of recent-onset type 1 diabetes patients. Thus, an examination on whether retrovirus particles are expressed in pancreatic tissues of type 1 diabetes patients was required to clarify the etiology of the onset of autoimmune type 1 diabetes.

Therefore, the present inventors have extensively examined the expression of retrovirus particles in pancreatic tissues of type 1 diabetes patients, and have found that retrovirus particles are expressed specifically in the pancreatic beta cells of diabetes patients. This fact can be exploited to develop a diagnosing reagent for type 1 diabetes and an immunogen. In particular 21 domains deduced from the above retroviral gene were elucidated to develop new peptides for vaccines and the like because these domains show hydrophilicity and immuno-dominancy.

The present inventors have also elucidated that the diabetes-specific retrovirus is an endogenous retrovirus (ERV-9) variant.

Although a direct relationship between the onset of type 1 diabetes and the expression of diabetes-specific endogenous retrovirus (ERV-9) was found, the role of beta cell-specific expression of retroviruses in the pathogenesis of beta cell-specific autoimmunity remains unknown. There are three possible mechanisms whereby retrovirus may be involved in the etiology of the disease.

First, the presentation of a retroviral antigen of the beta cells by MHC class II molecules from antigen-presenting cells (APCs), such as macrophages, may be the initial step in the autoimmune destruction of beta cells (Chomczynski P., et al., *Anal. Biochem.*, 162: 156, 1987; Froussard P. A., *Nucleic Acids Research*, 20(11): 2900, 1992; Shin A., et al., *J. virol.*, 63(1): 64–75, 1989). An immune response to a specific antigen on a target cell involves the activation of $CD4^+$ T cells, which are activated only when they interact with antigens presented on the surface of a macrophage or other APC.

Second, retroviral genome in the beta cells may alter the expression of cellular genes, possibly resulting in a beta cell-specific altered antigen(s) which could be recognized as foreign by the immune system. The retroviral antigen or altered beta cell antigen might be presented by MHC class I molecules and recognized as foreign by $CD8^+$ cytotoxic T cells (CTLs). Subsequently, signals transduced through T cell receptors (TcR) may be activated and CTLs may produce cytokines such as interferon-γ(INF-γ) which would, in turn, induce inflammation and further stimulate antigen presentation, leading to beta cell-specific autoimmunity (York I. A. and Rock K. L., *Annu. Rev. Immunol.*, 14: 369–396, 1996).

Third, retroviral antigen-specific effector T cells, which may recognize autoantigens expressed on the beta cells by molecular mimicry, may be generated.

SUMMARY OF THE INVENTION

The object of the present invention is to provide a whole genome of a diabetes-specific endogenous retrovirus (ERV-9) derived from the pancreatic tissues of type 1 diabetes patients, including the gag gene, pol gene, and env gene of the viral genome and their nucleotide sequences, shown in SEQ ID NO:1, SEQ ID NO:2, SEQ ID NO:4 and SEQ ID NO:6, respectively.

The object of the present invention is to provide amino acid sequences deduced from the above gene sequences. In particular, the Gag protein has the amino acid sequence shown in SEQ ID NO:3, the Pol protein has the amino acid sequence shown in SEQ ID NO:5 and the Env gene has the amino acid sequence shown in SEQ ID NO:7.

The object of the present invention is to provide antigens of the diabetes-specific endogenous retrovirus (ERV-9) containing the entire or partial amino acid sequence deduced from the above gag, pol or env gene sequences.

The object of the present invention is to provide antibodies for the diabetes-specific endogenous retrovirus (ERV-9), prepared by using the above antigens.

The object of the present invention is to provide vaccines for the diabetes-specific endogenous retrovirus (ERV-9) containing the above antigens as effective agents.

The object of the present invention is to provide diagnosing reagents for diabetes, which are prepared by using the above nucleotide sequences entirely and partially.

The object of the present invention is to provide diagnosing reagents for diabetes, which are prepared by using the entire or partial peptide sequences derived from Gag, Pol or Env protein.

The object of the present invention is to provide diagnosing reagents for diabetes, which are prepared by exploiting the above antibodies.

The object of the present invention is to provide a peptide and its derivative, which comprises the amino acid sequence containing the antigenic determinant or immuno-dominant domain deduced from the gene sequence of the diabetes-specific endogenous retrovirus (ERV-9).

The object of the present invention is to provide diagnosing reagents for diabetes, which contain the above peptide as an effective agent.

The object of the present invention is to provide antibodies for the diabetes-specific endogenous retrovirus (ERV-9), which are prepared by using the above peptide.

The object of the present invention is to provide vaccines for diseases related to the diabetes-specific endogenous retrovirus (ERV-9), which contain the above peptide as an effective agent.

DETAILED DESCRIPTION OF THE INVENTION

Figure 1:
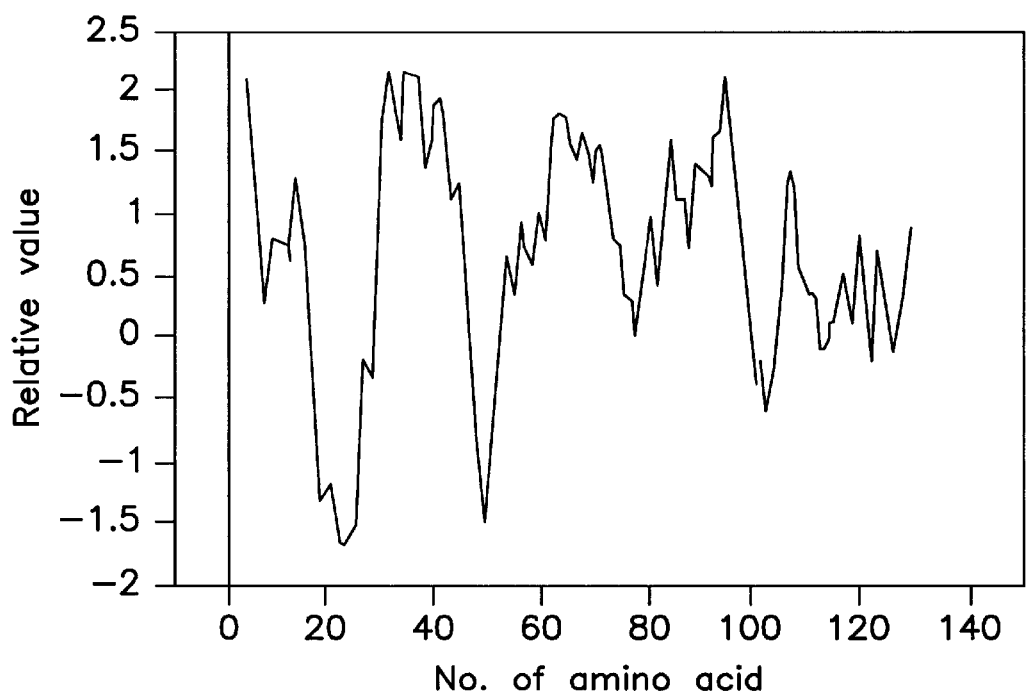
FIG. 1 is a graph showing the hydrophilicity/hydrophobicity of the peptide deduced from the gag gene sequence of a diabetes-specific endogenous retrovirus (ERV-9).

The present invention provides the genome of a diabetes-specific retrovirus, which is a variant of human endogenous retrovirus (ERV-9).

The diabetes-specific retrovirus of the present invention was purified from the pancreatic tissues of deceased type 1 diabetes patients and was identified to be expressed exclusively in pancreatic beta cells of the above patients. The nucleotide sequence of the gene is shown in SEQ ID NO:1.

The present invention provides diabetes-specific retroviral genes and their nucleotide sequences, which clarify that the retrovirus is a variant of a known human endogenous retrovirus (ERV-9). The nucleotide sequences of the gag gene, pol gene and env gene of the viral gene are shown in SEQ ID NO:2, SEQ ID NO:4, SEQ ID NO:6, respectively, wherein * is a termination codon.

In addition, the present invention provides amino acid sequences deduced from the above genes, by which 21 domains showing hydrophilicity and immuno-dominancy were identified. The Gag protein has the amino acid sequence shown in SEQ ID NO:3, the Pol protein has the amino acid sequence shown in SEQ ID NO:5, and the Env gene has the amino acid sequence shown in SEQ ID NO:7.

In detail, pancreata were obtained from four deceased, recent-onset type 1 diabetes patients and were embedded in paraffin. The embedded pancreata were sliced into sections and stained with hematoxylin-eosin (HE). In the sections, severe necrosis of the pancreatic islets with lymphocytic infiltration was observed, and lymphocytic destruction of the beta cells in the four patients was detected in all the pieces of each pancreas tail using electron microscopy. In addition, using the immunofluorescence method, the infiltrating lymphocytes were identified as $CD8^+$ T cells, $CD4^+$ T cells, macrophages and natural killer cells. The above retroviruses in the cytoplasm of the beta cells of the four diabetes patients were identified as C-type retrovirus particles, which are enveloped and spherical, with a diameter of about 120 nm and a dense central nucleoid. In contrast, other islet endocrine cells, such as alpha, delta and polypeptide-producing cells, as well as exocrine acinar cells, were intact and did not contain retrovirus particles. Retrovirus particles were not found in brain cells and spleen cells from the diabetes patients or normal controls.

Although the beta cell-specific expression of retrovirus particles was identified by electron microscopy, the sequences of the above retroviral gene found in the above diabetes patients and normal controls were determined because retrovirus particles could be present without detection in other tissues considering the limitations-of sectioning. As a result, a number of retroviral sequences were found to be present in both diabetes patients and normal controls. These common sequences were excluded from the type 1 diabetes-specific retrovirus. However, only one retroviral gene (particularly at the RNA level) was found in the pancreata from the four diabetes patients and not detected in the pancreata from normal controls. This viral gene sequence has homology with a human endogenous retroviral sequence (ERV-9; NIH GenBank Accession #85205).

In order to clone the whole genome of the diabetes-specific retrovirus, various primers were designed. First, using one primer from the above diabetes-specific sequence and another primer from the ERV-9 sequence, DNA fragments of 400 to 500 base pairs were amplified from a cDNA library of the pancreata of diabetes patients and cloned into a cloning vector, and the nucleotide sequences of the fragments were determined. Considering the sequence information, another primer was designed from the known sequence and the above processes were repeated in order to elucidate the whole gene sequences. As a result, it is known that the total number of nucleotides is 3910 and that this variant viral gene of the present invention has approximately 80% homology with a known human endogenous retrovirus (ERV-9) gene.

Comparing the diabetes-specific viral gene of the present invention with other retroviral gene, the structure of the gag, pol and env genes were determined, and amino acid sequences of the proteins were deduced from the above gene sequences. The antigenic determinant or immuno-dominant domain was detected and the hydrophilicity /hydrophobicity of the Gag, Pol and Env proteins were examined by analyzing the amino acid sequences. In particular, 21 domains of the viral proteins, having the amino acid sequences shown in SEQ ID NO: 8 to SEQ ID NO: 28 and their functional equivalents are identified to have hydrophilicity and immuno-dominancy. In the above SEQ ID NO: 8 to SEQ ID NO: 28, X can correspond to any amino acid available. In the above peptides, cysteine or an additional amino acid sequence such as Gly-Gly, Ser-Gly-Ser-Gly or the like can be added onto the N-terminus of the peptide. Amide (—NH$_2$), acetate (—COOH) or the like can be added onto the C-terminus of the peptide. The functional equivalents of the peptide can be selected from among analogue, complex, fragment, polymer, conjugate and mixture of the peptide having 21 domains. The above conjugate is a carrier protein conjugated peptide which is prepared by conjugating carrier protein onto the peptide with a disulfide bond, wherein the peptide has more than one of the 21 domains of peptide or the peptide by which an additional amino acid sequence such as Gly-Gly, Ser-Gly-Ser-Gly or the like is attached onto the N-terminus of the 21 domain peptide. The conjugate is also a biotin conjugated peptide which is prepared by conjugating biotin onto the 21 domain peptide by which an additional amino acid sequence such as Gly-Gly or Ser-Gly-Ser-Gly can be attached onto the N-terminus. The polymer is a branched form polymerized using poly-L-lysine resin such as Lys$_8$Lys$_4$Lys$_2$Lys-Y (wherein Y is amino acid or cysteine without —OH, —NH$_2$, branched functional group).

The present invention provides antigens of the diabetes-specific endogenous retrovirus (ERV-9) and antibodies for the antigen which can be prepared by using the peptide or the viral proteins derived from the above gene.

The present invention provides diagnosing reagents for diabetes or vaccines for diabetes which can be prepared by using the antigens and antibodies of the present invention. In addition, the above 21 domain peptides and their functional equivalents are provided, which can be synthesized by using the above sequences and the like and also can be exploited for diagnosing reagents for diabetes or vaccines for diabetes.

The present invention is further illustrated with reference to the following examples which are not intended to be in any way limiting to the scope of the invention as claimed.

EXAMPLE 1

Receipt of the pancreatic tissue samples

The present inventors received pancreata from four deceased, recent-onset type 1 diabetes patients. The first patient was a one year old girl, who died within one week of diagnosis of diabetes. There was no family history of autoimmune or endocrine diseases. The girl's blood glucose level was 406 mg/dl and her HLA type was DR3/14, DQ1/2. The second patient was a three year old girl, who lacked diabetes symptoms until she developed post-operative complications and severe hyperglycemia (a blood glucose level of 880 mg/dl). This patient's HLA type was DR1/7. The third and fourth patients were eight and ten year old boys, who both died of brain swelling during treatment for diabetes ketoacidosis shortly after diagnosis of type 1 diabetes. The ten non-diabetes control pancreata were obtained from the University of Calgary and the University of Alberta.

EXAMPLE 2

Observation of the pancreatic tissue samples

Examination of paraffin-embedded, hematoxylin-eosin (HE) stained sections of the pancreata from the four type 1 diabetes patients revealed severe necrosis of the pancreatic islets with lymphocytic infiltration. As a result of observation on the acetone-fixed frozen pancreatic tissues by the direct or indirect immuno-fluorescence method, using staining with monoclonal antibodies for leu M1 antigen and CD15 antigen for macrophages; leu2a antigen for CD4$^+$ T cells; leu 3a antigen for CD8$^+$ T cells; and leu 7 antigen and CD57 antigen for natural killer(NK) cells, the infiltrating immunocytes were determined to be CD8$^+$ T cells, CD4$^+$ T cells, macrophages and NK cells. Herein, CD4$^+$ T cells were slightly observed in patient 1 and both CD8$^+$ T cells and CD4$^+$ T cells were observed in patients 3 and 4. All four patients were found to be negative by indirect immunofluorescence using polyclonal antibody for rubella, CMV, Cox B4 virus and Parvo virus B19.

In part, lymphocytic destruction of beta cells in all four patients was revealed by the examination on an acetone-fixed ultra-thin piece of the tail of each pancreas by electron microscopy. That is, in patient 2, the nuclei of the beta cells were swollen and the chromatin was aggregated, and in other patients, the chromatin of the normal pancreatic duct cell was dense or pale. In addition, C-type retrovirus particles were found in the cytoplasm of intact or lymphocyte-infiltrated pancreatic beta cells of the four diabetes patients. The retrovirus was enveloped and spherical, with a diameter of about 120 nm and a dense central nucleoid. In contrast, other islet endocrine cells, which are alpha, delta and polypeptide-producing cells, as well as exocrine acinar cells, were intact and did not contain retrovirus particles. In addition, brain and spleen cells from diabetes patients or non-diabetic control subjects did not contain retrovirus particles.

EXAMPLE 3

RNA extraction from pancreatic tissue and synthesis of CDNA

The total RNA was extracted from frozen pancreatic tissue of the type 1 diabetes patients and healthy controls using the acid guanidium isothiocyanate-phenol chloroform extraction method, and the first cDNA strand was synthesized by the following method. The extracted RNA was dissolved in 4.4 $\mu$l of distilled water, to which 0.6 $\mu$l (20 units) of RNAsin, 4.3 $\mu$l of 5-fold concentrated Superscript buffer solution, 2 $\mu$l of mixed dNTPs (10 mM), 1 $\mu$l (200 ng) of Universal primer-dN6 (5'-GCCGGAGCTCTGCAGAA TTCNNNNNN-3') and 2.2 $\mu$l of DTT (50 mM) were added, heated at 65° C. for 5 minutes and immediately cooled in an ice bath. Secondly, 1.6 $\mu$l (16 units) of Superscript reverse transcriptase (Gibco BRL. Gaithersberg, Md., USA) was added and reacted at 37° C. for 1 hour. Then, the reaction-terminated mixture was centrifuged at 4° C., boiled at 100° C. for 2 minutes and immediately cooled in an ice bath.

Subsequently, the second cDNA strand was synthesized by the following method. To the above reaction-terminated mixture, 15 $\mu$l of distilled water, 10 $\mu$l of 5-fold concentrated Klenow buffer solution, 1 $\mu$l of dCTP and 1.5 $\mu$l (9 units) of Klenow enzyme were added, centrifuged momentarily at 4° C. and maintained at 37° C. for reaction. The excess Universal primer-dN6 was cleared off by the process in which, after 200 $\mu$l of distilled water was added to the above reaction-terminated mixture, the mixture was passed through a Cetri-Sep™ spin column (Princeton Separations, Inc., Adelphia, N.J., U.S.A.) and centrifuged at 4000 rpm for 5 minutes.

PCR was performed by the following process in order to amplify the double-helical cDNA synthesized at random: 10 $\mu$l of 10-fold concentrated PCR buffer solution (Perkin Elmer, U.S.A.), 6 $\mu$l of 25 mM magnesium chloride solution, 500 $\mu$M of each dNTP, 1 $\mu$l of Universal primer (200 ng) and 0.5 $\mu$l (2.5 units) of Taq DNA synthesis enzyme (Gibco BRL, Gaithersberg, Md., U.S.A.) were added to the above cDNA solution to adjust the final reaction volume to 100 $\mu$l. An equal volume of mineral oil was layered on the surface of the reactant solution and the cDNA was amplified for 35 cycles at 94° C. for 1 min, 55° C. for 1 min and 72° C. for 2 min using a TR-96 model heating incubator.

EXAMPLE 4

Cloning of the retrovirus gene

The reverse transcriptase gene fragment from the cDNA library of <Example 3> was amplified using a mixed oligo-nucleotide primer (MOP) of the following sequence derived from the conserved region of the reverse transcriptase gene:

5'-TGGAAAGTG(T,C)T(G,A)CC(A,C)CA(A,G)GG-3'
3'-ATG(T,C)ACCTACTG(T,G)A(G,C)GACGACCGG(A,C)GG-5'

After the amplified gene was electrophoresed on an agarose gel followed by staining with ethidium bromide, the band with a length of 138 base pairs was cut and the gene fragment was extracted from the gel by the electro-extraction method. 6 μl of distilled water, 1 μl of 10-fold concentrated ligase buffer solution, 1 μl of T4 ligase and 2 μl (50 ng) of pCRII™ vector (TA cloning kit, Invitrogen, Carlsbad, Calif., U.S.A.) were added to 1 μl of the extracted reverse transcriptase gene and reacted at 12° C. for 12 hours (overnight). Subsequently, 1 μl of the above ligation reaction mixture was mixed with INVaF' strain and cooled in an ice bath for 30 min in order to transform the INVaF' strain with a pCRII™ vector cloned with a reverse transcriptase gene. Subsequently, the mixture was reacted in a 45° C. water bath for exactly 45 seconds and cooled in an ice bath for 2 min. Next, 450 μl of SOC media was added to each reaction tube and the tubes were incubated at 37° C. for 1 hour. Next, 100 μl of transformed cell suspension was layered on LB agarose plates containing 50 μl of ampicillin (50 μg/ml) and 50 μl of X-Gal (20 mg/ml) and the plates were incubated at 37° C.

EXAMPLE 5

Sequencing of the retroviral gene 308 colonies containing viral gene fragments of 138 base pairs were obtained from <Example 4> and sequenced using a sequenase 2.0 kit (US Biochemicals) and a Taq Dideoxy™ terminator cycling sequence kit (Perkin Elmer, Foster City, Calif., U.S.A.) with 373A sequence analyzer (Applied Biosystem). The homology between the above analyzed sequence and the known nucleotide sequence was examined through the GenBank Data Base (NIH, USA), and it was found that the diabetes-specific nucleotide sequences from the four diabetes patients have approximately 85% homology with a known endogenous retrovirus gene (GenBank accession number #85205).

Next, by the following process, sequencing of the entire retrovirus gene was completed. One primer from the diabetes-specific sequence and one primer from the ERV-9 sequence were designed to amplify a 400 to 500 base pair fragment. After amplification of the diabetes patients' cDNA library with these two primers, the fragments were cloned into a PCRII™ vector (Invitrogen, U.S.A.) and sequenced. By considering the sequence information, a primer was designed from the known sequence and the above processes were repeated in order to elucidate the whole gene sequences.

As a result, the total number of nucleotides was found to be 3910 and this variant viral gene was shown to have approximately 80% homology with a known human endogenous retrovirus (ERV-9) gene (SEQ ID NO:1). In addition, by comparing the diabetes-specific variant viral gene of ERV-9 with another retroviral gene, the site and the structure of the gag, pol and env genes were determined. The gag gene corresponds to nucleotides 1 to 396 of the variant viral gene, the pol gene corresponds to nucleotides 397 to 2726 and the env gene corresponds to nucleotides 2858 to 3322.

EXAMPLE 6

Sequencing of the amino acids

Figure 2:
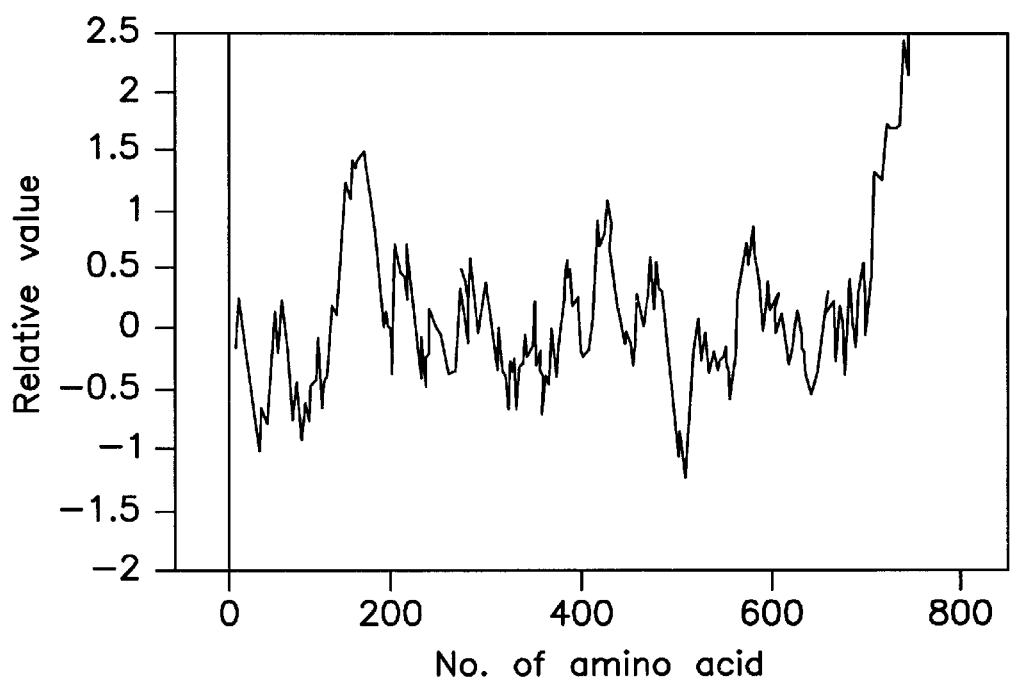
FIG. 2 is a graph showing the hydrophilicity/hydrophobicity of the peptide deduced from the pol gene sequence of a diabetes-specific endogenous retrovirus (ERV-9).
Figure 3:
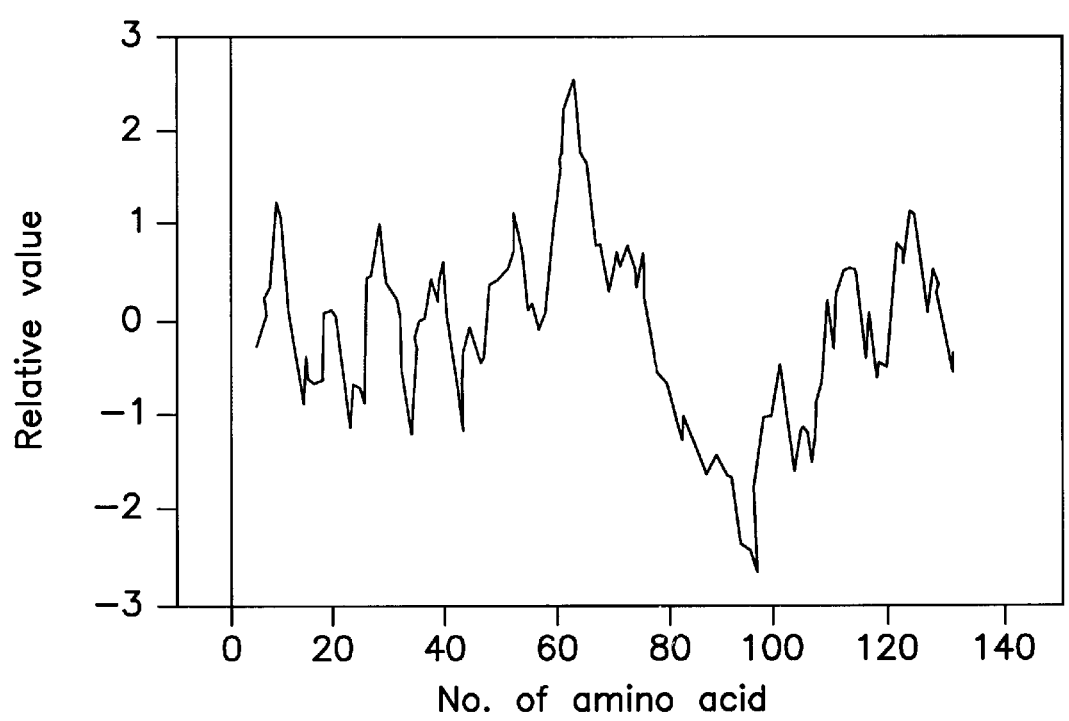
FIG. 3 is a graph showing the hydrophilicity/hydrophobicity of the peptide deduced from the env gene sequence of a diabetes-specific endogenous retrovirus (ERV-9).

The present inventors deduced the amino acid sequence of the protein produced according to the induced gene structure (SEQ ID NO: 3, 5, 7. Herein, * is deduced from termination codon). Therefore, the antigenic determinant domain or immunodominant domain was examined by analyzing amino acid sequences and the hydrophilicity/hydrophobicity was examined from each amino acid sequences of the gag (SEQ ID NO: 3), pol (SEQ ID NO: 5) and env (SEQ ID NO: 7) genes shown in FIG. 1, FIG. 2 and FIG. 3.

As a result, the following 21 domains were expected to have hydrophilicity and immuno-dominancy (SEQ ID NO: 8 to SEQ ID NO: 28).

In the above SEQ ID NO: 8 to SEQ ID NO: 28, X can correspond to any amino acid.

EFFECT OF THE INVENTION

As distinctly described above, the present invention provides the nucleotide sequences of the endogenous retrovirus variant (ERV-9) gene purified from pancreatic tissues of type 1 diabetes patients in which the viral gene is expressed specifically and also provides the amino acid sequences derived from the above viral genes. By analyzing the above sequences, 21 domains of the viral proteins are identified to have hydrophilicity and immuno-dominancy. Therefore, the peptide and its derivatives containing the above domains and the viral protein prepared by using the variant viral genes of the present invention can be utilized to develop antigens for the diabetes-specific virus. The above antigens can be used for diagnosing autoimmune antibodies of type 1 diabetes. In addition, vaccines for the variant ERV-9-related diseases can be developed by exploiting the above protein and peptides effectively.

What is claimed is:

1. An isolated and purified diabetes-specific endogenous retrovirus (ERV-9) nucleic acid comprising the nucleotide sequence set forth in SEQ ID NO:1.

2. An isolated and purified diabetes-specific endogenous retrovirus (ERV-9) nucleic acid comprising the gag gene set forth in SEQ ID NO:2.

3. An isolated and purified diabetes-specific endogenous retrovirus (ERV-9) nucleic acid comprising the pol gene set forth in SEQ ID NO:4.

4. An isolated and purified diabetes-specific endogenous retrovirus (ERV-9) nucleic acid comprising the env gene set forth in SEQ ID NO:6.

* * * * *